(12) United States Patent
Quest et al.

(10) Patent No.: US 7,389,874 B2
(45) Date of Patent: Jun. 24, 2008

(54) HEART VALVE SUPPORT AND STORING LID SYSTEM AND METHODS ASSOCIATED THEREWITH

(75) Inventors: Matthew Quest, Bothell, WA (US); Bob Allan, Maple Grove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 233 days.

(21) Appl. No.: 11/183,537

(22) Filed: Jul. 18, 2005

(65) Prior Publication Data

US 2006/0015177 A1    Jan. 19, 2006

Related U.S. Application Data

(60) Provisional application No. 60/589,427, filed on Jul. 19, 2004.

(51) Int. Cl.
*A61B 17/06* (2006.01)
*B65D 85/30* (2006.01)
*A61F 2/24* (2006.01)

(52) U.S. Cl. .................. 206/438; 206/210; 206/363; 623/2.1

(58) Field of Classification Search ............... 206/438, 206/363, 205–210, 364, 349, 477, 486–487; 623/2.1–2.11
See application file for complete search history.

(56) References Cited

U.S. PATENT DOCUMENTS

| | | | |
|---|---|---|---|
| 3,409,013 A | 11/1968 | Berry | |
| 3,628,535 A | 12/1971 | Ostrowsky et al. | |
| 3,666,088 A | 5/1972 | Wingardh | |
| 3,959,827 A | 6/1976 | Kaster | |
| 4,182,446 A | 1/1980 | Penny | |
| 4,211,325 A | 7/1980 | Wright | |
| 4,506,394 A | 3/1985 | Bedard | |
| 4,542,825 A * | 9/1985 | Thomas et al. | 206/363 |
| 4,585,453 A | 4/1986 | Martin et al. | |
| 4,655,218 A | 4/1987 | Kulik et al. | |
| 4,679,556 A | 7/1987 | Lubock et al. | |

(Continued)

FOREIGN PATENT DOCUMENTS

EP     0246086 A2    11/1987

(Continued)

OTHER PUBLICATIONS

US 5,961,551, Chasak et al. (withdrawn).

(Continued)

*Primary Examiner*—Bryon P Gehman
(74) *Attorney, Agent, or Firm*—Ropes & Gray LLP; Stuart Yothers; Robert R. Jackson

(57) ABSTRACT

Systems and methods for supporting a replacement heart valve are presented herein. A bioprosthesis may be stored in a storage container by suspending the bioprosthesis from a support structure. The volume of storage solution may be reduced by using a lid with a boss extending therefrom to displace some of the volume of the storage container. The support structure may rest on the base of the storage container. Additionally, there may be a holder attached to the bioprosthesis above the support structure. The holder-bioprosthesis-support structure may be constrained between the lid and base of the storage container.

15 Claims, 19 Drawing Sheets

U.S. PATENT DOCUMENTS

| | | | |
|---|---|---|---|
| 4,697,703 A * | 10/1987 | Will | 206/438 |
| 4,702,250 A | 10/1987 | Ovil et al. | |
| 4,705,516 A | 11/1987 | Barone et al. | |
| 4,755,181 A | 7/1988 | Igoe | |
| 4,801,015 A | 1/1989 | Lubock et al. | |
| 4,838,288 A | 6/1989 | Wright et al. | |
| 4,865,600 A | 9/1989 | Carpentier et al. | |
| 4,878,494 A | 11/1989 | Phillips et al. | |
| 4,881,562 A | 11/1989 | Wright et al. | |
| 4,932,965 A | 6/1990 | Phillips | |
| 5,061,277 A | 10/1991 | Carpentier et al. | |
| 5,089,015 A | 2/1992 | Ross | |
| 5,197,979 A | 3/1993 | Quintero et al. | |
| 5,236,450 A | 8/1993 | Scott | |
| 5,290,300 A | 3/1994 | Cosgrove et al. | |
| 5,336,258 A | 8/1994 | Quintero et al. | |
| 5,350,420 A | 9/1994 | Cosgrove et al. | |
| 5,403,305 A | 4/1995 | Sauter et al. | |
| 5,443,502 A | 8/1995 | Caudillo et al. | |
| 5,476,510 A | 12/1995 | Eberhardt et al. | |
| 5,496,336 A | 3/1996 | Cosgrove et al. | |
| 5,531,785 A | 7/1996 | Love et al. | |
| 5,560,487 A | 10/1996 | Starr | |
| 5,571,175 A | 11/1996 | Vanney et al. | |
| 5,578,076 A | 11/1996 | Krueger et al. | |
| 5,628,789 A | 5/1997 | Vanney et al. | |
| 5,690,654 A | 11/1997 | Ovil | |
| 5,695,503 A | 12/1997 | Krueger et al. | |
| 5,713,951 A | 2/1998 | Garrison et al. | |
| 5,713,952 A | 2/1998 | Vanney et al. | |
| 5,716,401 A | 2/1998 | Eberhardt et al. | |
| 5,716,402 A | 2/1998 | Reif | |
| 5,720,391 A | 2/1998 | Dohm et al. | |
| 5,728,153 A | 3/1998 | Menkis et al. | |
| 5,735,842 A | 4/1998 | Krueger et al. | |
| 5,735,894 A | 4/1998 | Krueger et al. | |
| 5,776,187 A | 7/1998 | Krueger et al. | |
| 5,800,531 A | 9/1998 | Cosgrove et al. | |
| 5,807,405 A | 9/1998 | Vanney et al. | |
| 5,814,097 A | 9/1998 | Sterman et al. | |
| 5,814,101 A | 9/1998 | Wallner et al. | |
| 5,823,342 A | 10/1998 | Caudillo et al. | |
| 5,824,068 A | 10/1998 | Bugge | |
| 5,855,602 A | 1/1999 | Angell | |
| 5,868,253 A | 2/1999 | Krueger et al. | |
| 5,871,489 A | 2/1999 | Ovil | |
| 5,876,437 A | 3/1999 | Vanney et al. | |
| 5,904,695 A | 5/1999 | Krueger | |
| 5,906,642 A | 5/1999 | Caudillo et al. | |
| 5,908,450 A | 6/1999 | Gross et al. | |
| 5,954,709 A | 9/1999 | Campbell et al. | |
| 5,957,976 A | 9/1999 | Vanney et al. | |
| 5,964,800 A | 10/1999 | Sparks et al. | |
| 5,972,030 A | 10/1999 | Garrison et al. | |
| 5,980,569 A | 11/1999 | Scirica | |
| 5,984,959 A | 11/1999 | Robertson et al. | |
| 6,019,790 A | 2/2000 | Holmberg et al. | |
| 6,090,138 A | 7/2000 | Chasak et al. | |
| 6,096,074 A | 8/2000 | Pedros | |
| 6,126,007 A | 10/2000 | Kari et al. | |
| 6,197,053 B1 | 3/2001 | Cosgrove et al. | |
| 6,199,696 B1 | 3/2001 | Lytle et al. | |
| 6,200,306 B1 | 3/2001 | Klostermeyer et al. | |
| 6,214,043 B1 | 4/2001 | Krueger et al. | |
| 6,283,993 B1 | 9/2001 | Cosgrove et al. | |
| 6,358,240 B1 | 3/2002 | Campbell et al. | |
| 6,409,758 B2 | 6/2002 | Stobie et al. | |
| 6,416,547 B1 | 7/2002 | Erickson et al. | |
| 6,540,782 B1 | 4/2003 | Snyders | |
| 6,558,416 B2 | 5/2003 | Cosgrove et al. | |
| 6,558,418 B2 | 5/2003 | Carpentier et al. | |
| 6,564,805 B2 | 5/2003 | Garrison et al. | |
| 6,591,998 B2 * | 7/2003 | Haynes et al. | 206/438 |
| 6,613,085 B1 | 9/2003 | Anderson et al. | |
| 6,702,852 B2 | 3/2004 | Stobie et al. | |
| 6,723,122 B2 | 4/2004 | Yang et al. | |
| 6,736,845 B2 | 5/2004 | Marquez et al. | |
| 6,802,860 B2 | 10/2004 | Cosgrove et al. | |
| 2002/0082686 A1 | 6/2002 | Nguyen-Thein-Nhon et al. | |
| 2002/0161431 A1 | 10/2002 | Stobie et al. | |
| 2003/0125805 A1 | 7/2003 | Johnson et al. | |

FOREIGN PATENT DOCUMENTS

| | | |
|---|---|---|
| EP | 0242172 B1 | 1/1992 |
| EP | 0735845 B1 | 7/2002 |
| FR | 1005345 | 4/1952 |
| GB | 2102681 A | 2/1983 |
| GB | 2108393 A | 5/1983 |
| SU | 1008937 | 7/1984 |
| SU | 1621912 | 1/1991 |
| WO | WO 89/04145 | 5/1989 |
| WO | WO 92/03990 A1 | 3/1992 |
| WO | WO 92/12688 A1 | 8/1992 |
| WO | WO 92/21298 A1 | 12/1992 |
| WO | WO 95/14443 A1 | 6/1995 |
| WO | WO 95/17139 A1 | 6/1995 |
| WO | WO 98/14138 A1 | 4/1998 |
| WO | WO 99/37248 A1 | 7/1999 |
| WO | WO 00/40176 A1 | 7/2000 |
| WO | WO 02/09621 A2 | 2/2002 |

OTHER PUBLICATIONS

US 6,197,052, Cosgrove et al. (withdrawn).

* cited by examiner

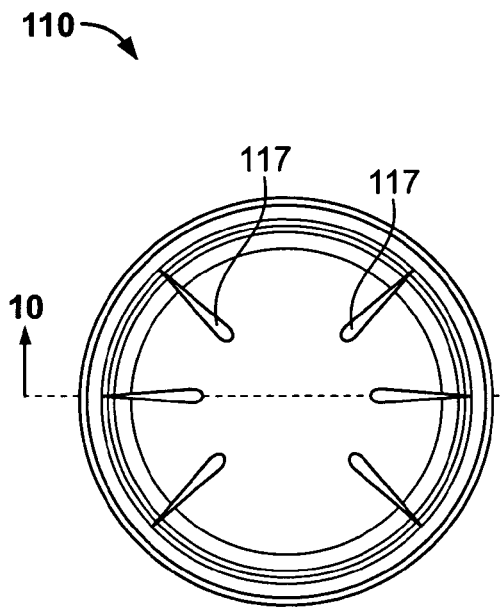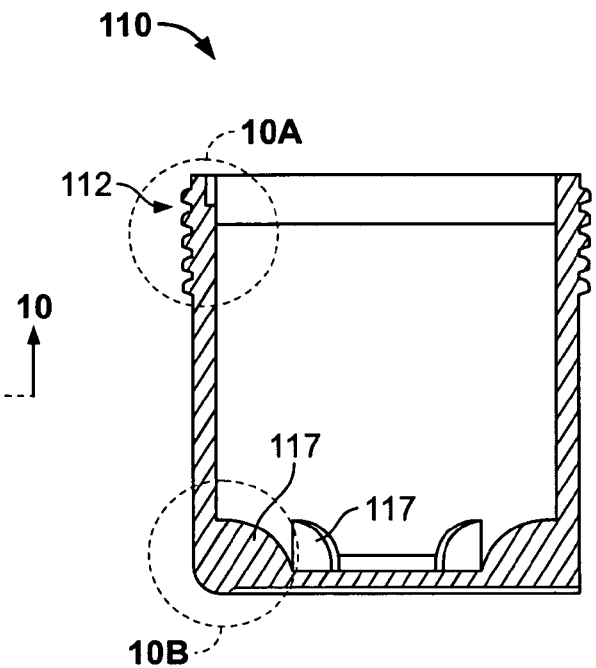
FIG. 9  FIG. 10
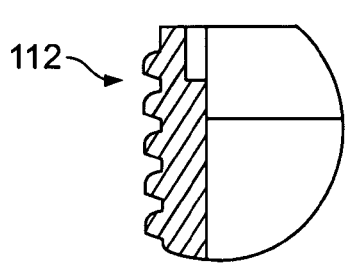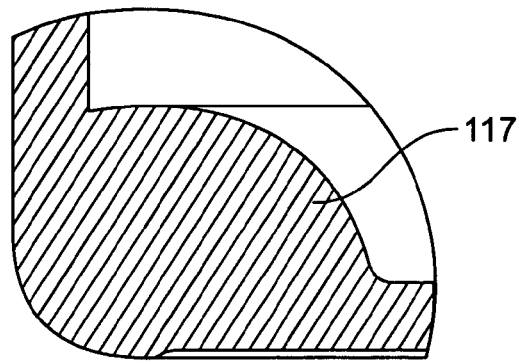
FIG. 10A  FIG. 10B

HEART VALVE SUPPORT AND STORING LID SYSTEM AND METHODS ASSOCIATED THEREWITH

This application claims the benefit of U.S. provisional patent application No. 60/589,427, filed Jul. 19, 2004, which is hereby incorporated by reference herein in its entirety.

BACKGROUND OF THE INVENTION

This invention relates generally to systems and methods for storing and delivering bioprosthetic heart valves. Systems and methods in accordance with the principles of the present invention may be used for storing and transporting bioprosthetic replacements for any of the heart's valves (e.g., aortic, mitral, pulmonary, and tricuspid). Bioprosthetic replacements such as supra valves may also be stored and transported in accordance with the principles of the present invention. A supra valve may take the place of or supplement the function of the aortic valve, but may be implanted slightly higher in a patient's aorta than an aortic valve. Several disadvantages to current bioprosthetic storage and delivery procedures are addressed by the present invention.

Presently, bioprosthetic heart valves are stored in a solution that must be rinsed off before the valve can be implanted. The valve is suspended in a solution to preserve the tissue of the bioprosthesis. Typically, this solution is either formaldehyde-based or gluteraldehyde-based and care must be exercised in the operating room not to contaminate the sterile operating field with the storage solution.

However, current bioprosthetic heart valve packaging requires the removal of the valve from the storage container before the holder handle may be attached (i.e., the scrub nurse or surgeon may have to reach into the storage solution to retrieve the valve and then remove the structure that was supporting the valve in the jar). Because the jar is completely filled with the storage solution, these cumbersome steps have the potential to contaminate the gloves of the person retrieving the valve. Furthermore, the potential for spilling storage solution in the operating room is high, because the jar is completely filled with storage solution.

The step of rinsing the valve can be problematic in its own right, because this procedure takes at least six minutes. During these six minutes, a scrub nurse must continue to provide the surgeon with instruments, sutures, etc. However, he or she may also be responsible for rinsing the valve. Resting the valve in the rinse basin may damage the valve, and the rinse process may require the rinser to agitate the rinse solution. Thus, the scrub nurse must attend to both the surgeon and the valve rinse procedure. Furthermore, the valve may stay in the final rinse basin for an extended period if the surgeon is not ready for the valve when the final rinse is complete. Finally, some operating room personnel prefer to attach the holder handle to the valve holder while the valve is resting in the sterile field. For these reasons, it may be desirable to provide a device that would protect the valve if it were set down during the operation.

Therefore, it is an object of the present invention to provide a heart valve holder and support assembly that could be allowed to rest in the rinse basin during the rinse procedure without having to worry about damaging the valve. Additionally, it is an object of the present invention to reduce the likelihood of spilling storage solution in the operating room and of contaminating any of the persons or surfaces in the operating room.

A heart valve support and lid liner system directed to these objectives may be implemented with existing heart valve products such as St. Jude Medical's Biocor and Epic heart valve product lines. However, it should be understood that such support and lid liner systems could be adapted to any existing or future heart valve product lines.

SUMMARY OF THE INVENTION

Valve supports in accordance with the present invention allow the holder handle to be attached to the valve holder as soon as the lid of the jar is removed and while the valve/holder/support assembly is still inside the jar. Supports in accordance with the present invention may be left on the valve until just before the surgeon implants the valve, protecting the valve until it is needed. Such supports may simplify the operating room procedure because the scrub nurse does not have to remove the valve/holder/support from the jar nor remove the support from the valve before attaching the handle. The support may also eliminate the contamination of the scrub nurse's gloves by the storage solution, which is more likely to occur if the scrub nurse removes the valve from the jar by hand. Such a support may additionally eliminate contamination of an instrument and the risk of dropping the valve if the scrub nurse removes the valve from the jar with an instrument.

One embodiment of the present invention comprises a clip-like device (e.g., a grip) that attaches to the sewing cuff of a replacement heart valve and supports the valve from below. Supporting the valve in this manner allows the scrub nurse or surgeon to thread the holder handle directly into the valve holder as soon as the lid is removed from the jar. The valve support may remain attached to the replacement valve to protect it until the surgeon is ready to perform the implant procedure.

In order to secure the valve in the jar vertically, a lid liner with a protrusion in the center may be used to hold the heart valve holder and support assembly in place. This protrusion attaches to the lid and may take up volume within the jar, enabling the use of less storage solution. Therefore, when the lid and lid liner are removed, the fluid level in the jar drops and the fluid is not as likely to spill in the operating room.

BRIEF DESCRIPTION OF THE DRAWINGS

Further features of the invention, its nature, and various advantages will be more apparent from the following detailed description and the accompanying drawings, in which:

FIG. 9 is a perspective view of an illustrative embodiment of apparatus in accordance with the principles of the present invention.

FIG. 10 is a cross-sectional view of the apparatus shown in FIG. 9 taken from line 10-10 of FIG. 9.

FIG. 10A is a view similar to FIG. 10 showing an enlarged view of detail A of FIG. 10.

FIG. 10B is a view similar to FIG. 10 showing an enlarged view of detail B of FIG. 10.

DETAILED DESCRIPTION OF THE PREFERRED EMBODIMENTS

Figure 1:
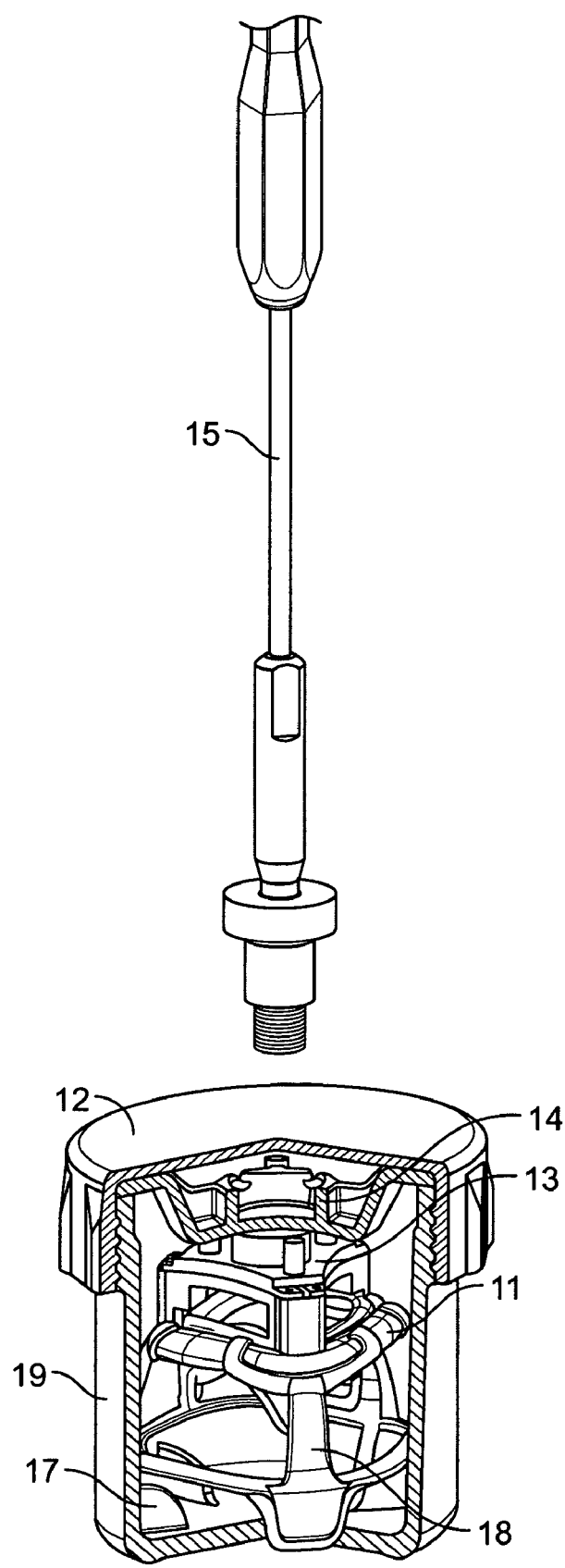
FIG. 1 is a cutaway perspective view of an illustrative embodiment of apparatus in accordance with the principles of the present invention.

Illustrative apparatus in accordance with the principles of the present invention are illustrated in FIG. 1. Such apparatus may include jar 19 and lid 12 to store and transport a heart valve prosthesis that has been prepared for surgical implant. Lid 12 may be fitted with lid liner 14. Heart valve 11 may be attached to valve holder 13 and support 18. When valve holder 13, heart valve 11, and support 18 are assembled within jar 19 as shown in FIG. 1, heart valve 11 is suspended within jar 19 by being vertically constrained between lid liner 14 and the base of jar 19. The heart valve holder and support assembly may be rotationally constrained by tabs 17 in the base of jar 19.

In general, jar 19 contains heart valve 11 with support 18 resting on the base of jar 19 and valve holder 13 resting above heart valve 11. However, the orientation of heart valve 11 may vary depending on the intended use. For example, a replacement mitral valve may be stored (i.e., held) with the valve leaflets and commissure posts extending downwardly from the level of the valve's sewing cuff, whereas aortic and supra valves may be held with the valve leaflets and commissure posts extending upwardly from the level of the valve's sewing cuff.

Valve holder 13 may include an internal rotating mechanism to deflect the lower ends of the commissure posts radially inward. In the case of a replacement mitral valve, valve holder 13 may engage the sewing cuff of replacement heart valve 11 at locations annularly spaced around the valve. When holding aortic and supra replacement valves, valve holder 13 may be designed to engage the ends of the commissure posts of the replacement heart valve.

Heart valve 11 should be packaged such that the entire prosthesis is always completely immersed in the storage solution. This is typically achieved by completely filling jar 19 with storage solution. However, lid liner 14 may be designed to displace some of the volume of jar 19. Thus, jar 19 does not have to be completely filled with storage solution to ensure total immersion of heart valve 11. Apparatus in accordance with the principles of the present invention may also include holder handle 15.

Figure 2:
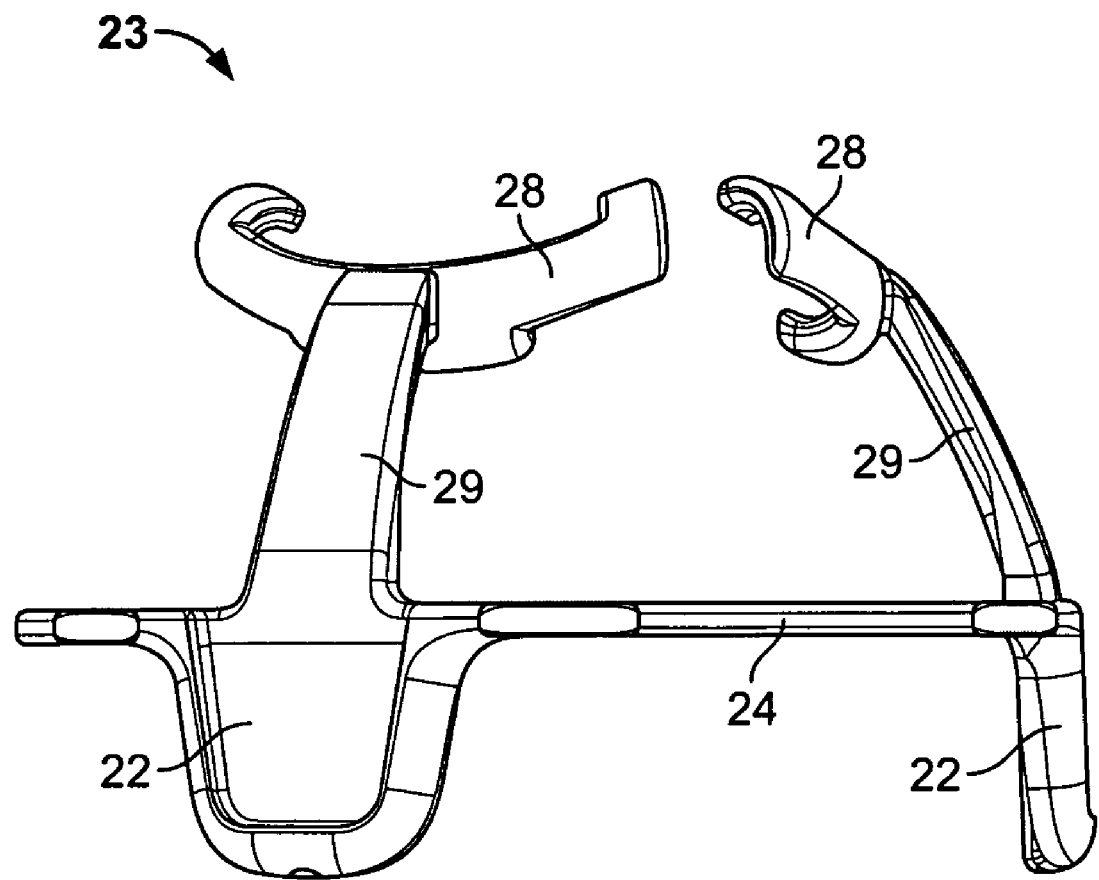
FIG. 2 is a perspective view of an illustrative embodiment of apparatus in accordance with the principles of the present invention.

An enlarged detailed view of one embodiment of a support is shown in FIG. 2. Support 23 (which may be used as support 18 of FIG. 1) may include finger tabs 22, ring 24, struts 29, and grips 28. Grips 28 may be designed to grip the sewing cuff or other suitable gripping surface of a prosthetic heart valve. Finger tabs 22 may be squeezably operable to release grips 28 from a supported prosthetic heart valve. Additionally, finger tabs 22 may provide resting support for support 23 within jar 19. Ring 24 may protect a stored heart valve from colliding with the wall of jar 19 if jar 19 is dropped or subjected to some other form of shock or impact.

Support 23 may attach directly to the sewing cuff of heart valve 11. Support 23 may alternatively be attached to valve holder 13. Some heart valve support products support the holder from above, obstructing the handle attachment means when the storage container is opened. Thus, to attach a handle to the replacement valve and holder, the support must first be removed. Support 23 may support a heart valve from below, and may engage a feature of the replacement valve instead of the holder. This feature enables immediate handle attachment and eliminates the codependence of the holder and support, allowing either component to be changed without affecting the other.

Supports like support 23 may be adapted for one-step removal. In such designs, ring 24 which connects three upstanding struts 29 may act as a pivot point. When finger tabs 22 below ring 24 are pressed toward the flow axis of the valve, grips 28 rotate away from the valve's sewing cuff or other engagement surface and release the valve. This feature simplifies the operating room procedure as current valve supports require a more complex method to remove the support from the valve (e.g., multiple disassembly steps, cutting a suture, etc.).

Figure 3:
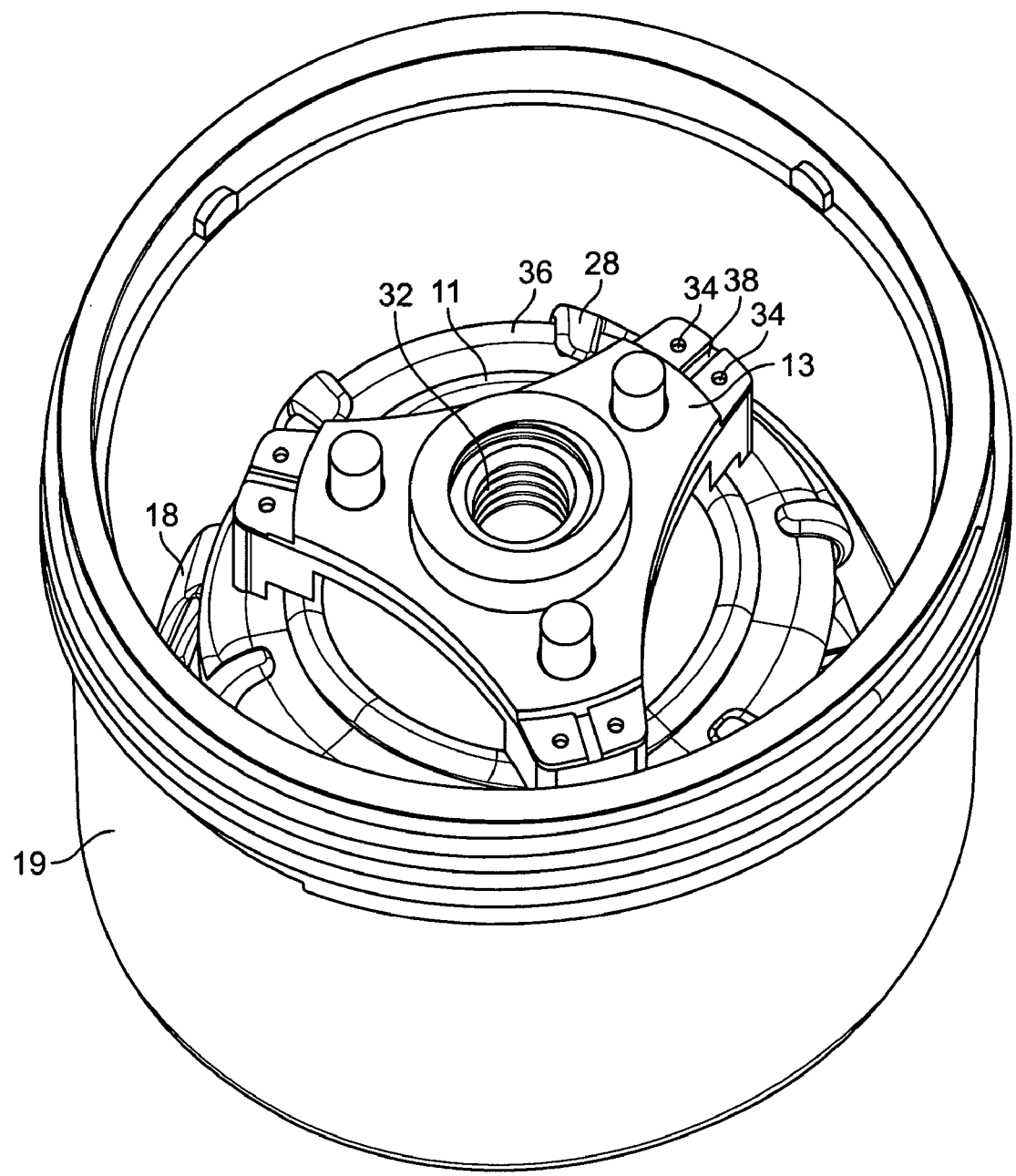
FIG. 3 is a view similar to FIG. 1 showing an enlarged view of the apparatus illustrated in FIG. 1 and showing a portion of a particular illustrative procedure and related apparatus in accordance with the invention.

FIG. 3 illustrates heart valve 11 with holder 13 and support 18 attached by grips 28 after the lid and lid liner have been removed from jar 19. Holder 13 may be attached to valve 11 by sutures that pass through eyelets 34 and sewing cuff 36. Holder 13 may have cutting grooves 38 so that sutures securing valve 11 to holder 13 can be easily cut at the appropriate time to remove valve 11 from holder 13. As shown in FIG. 3, holder 13 may include threads 32 for the attachment of holder handle 15 (see FIG. 1).

Figure 4:
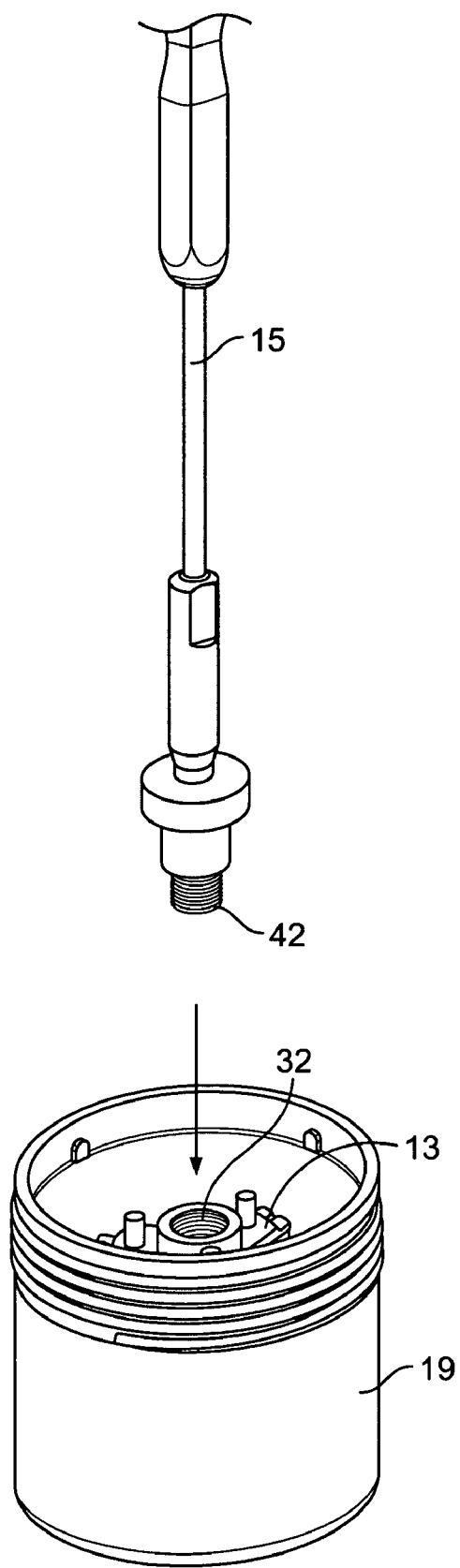
FIG. 4 is a view similar to FIG. 1 showing a later stage in the illustrative procedure depicted in part by FIG. 3, together with related apparatus, all in accordance with this invention.

As shown in FIG. 4, holder handle 15 is threaded into valve holder 13 such that threads 42 of holder handle 15 threadably engage threads 32 of valve holder 13. This secures valve/holder/support assembly 50 (see FIG. 5) to holder handle 15. Because threads 32 are exposed upon the removal of the combined lid and lid liner, there is no reason for the scrub nurse or surgeon to actually reach into jar 19 with their sterile, gloved hands. Holder handle 15 is inserted directly into jar 19 to remove assembly 50 (see FIG. 5) from jar 19. Alternatively, holder handle 15 may snap into holder 13, or any other suitable attachment mechanism may be used.

Figure 21:
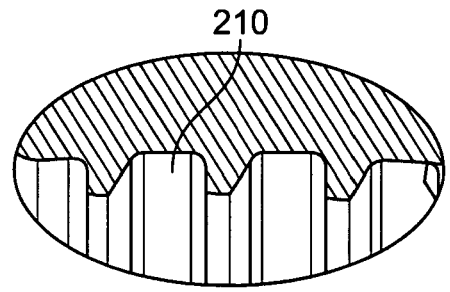
FIG. 21 is an enlarged detailed cross-sectional view of the apparatus shown in FIG. 19 taken from line 21-21 of FIG. 19.
Figure 22:
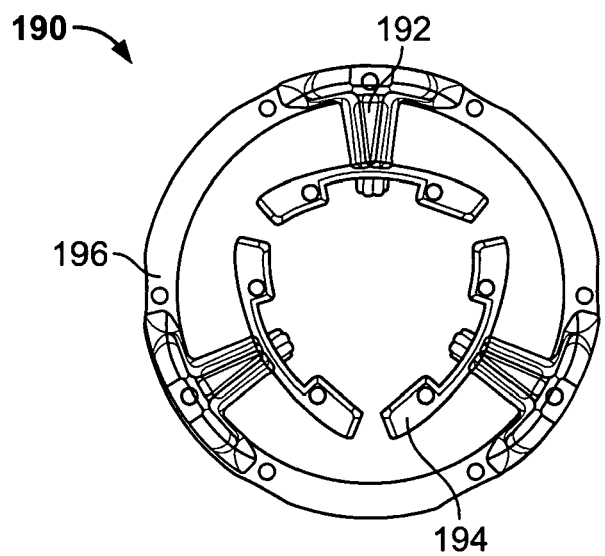
FIG. 22 is a perspective view of an illustrative embodiment of apparatus in accordance with the principles of the present invention.
Figure 23:
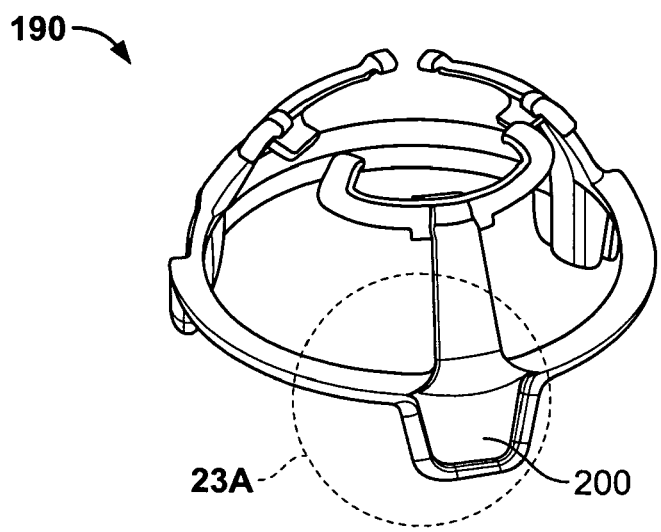
FIG. 23 is an isometric view of the apparatus shown in FIG. 22.
Figure 23A:
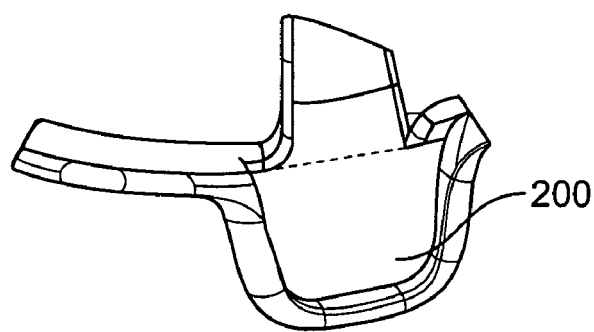
FIG. 23A is a view similar to FIG. 23 showing an enlarged view of detail A of FIG. 23.

Because holder handle 15 is threaded into valve holder 13, it is important that support 18 is able to hold the valve securely while holder handle 15 is tightened. To increase the torsional force that can be applied to valve holder 13 before sewing cuff 36 would begin to slip through grips 28 of support 18 (e.g., rotate about the holder handle axis and slide through the grips), small ridges (see, e.g., ridges 210 of FIG. 21) may be added to grips 28.

Figure 5:
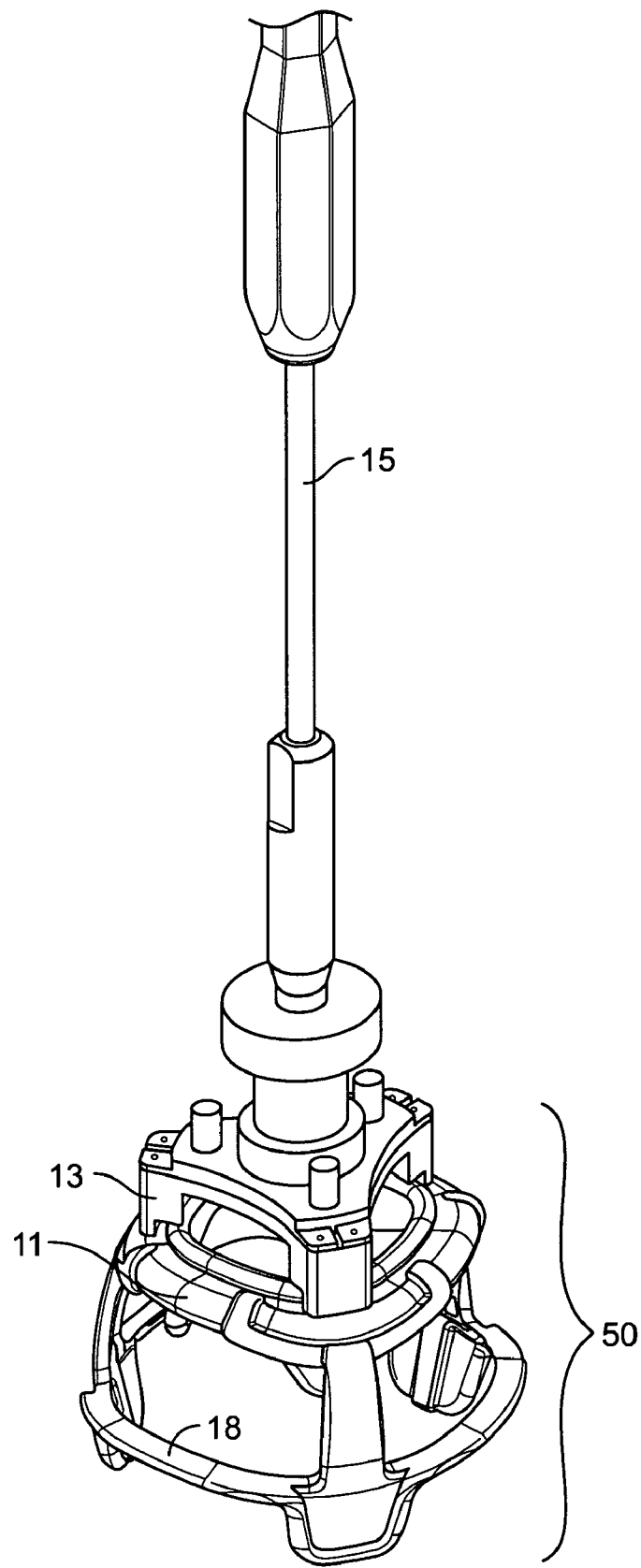
FIG. 5 shows an even later stage in the illustrative procedure depicted in part by FIGS. 3 and 4, together with related apparatus, all in accordance with this invention.

FIG. 5 illustrates assembly 50 removed from jar 19 (not shown). Assembly 50 may include support 18, heart valve 11, and holder 13. Once assembly 50 is removed, heart valve 11 is rinsed. A preferred rinse procedure may include filling three sterile basins with sterile isotonic saline. Assembly 50 and the portion of holder handle 15 that was submerged in the valve storage solution should be fully immersed in the sterile isotonic saline solution of the first basin. The valve may be rinsed in the first basin for a fixed period of time with a gentle back and forth motion. The rinse process may be repeated in each of the three basins. Once the rinse procedure is completed, assembly 50 may be left immersed in the third basin until the surgeon is ready for implantation. Preferably, all of assembly 50 is rinsed, so that everything in FIG. 5 is sterile and free of aldehyde residuals (or toxic residuals) and ready for the operating environment.

Figure 6:
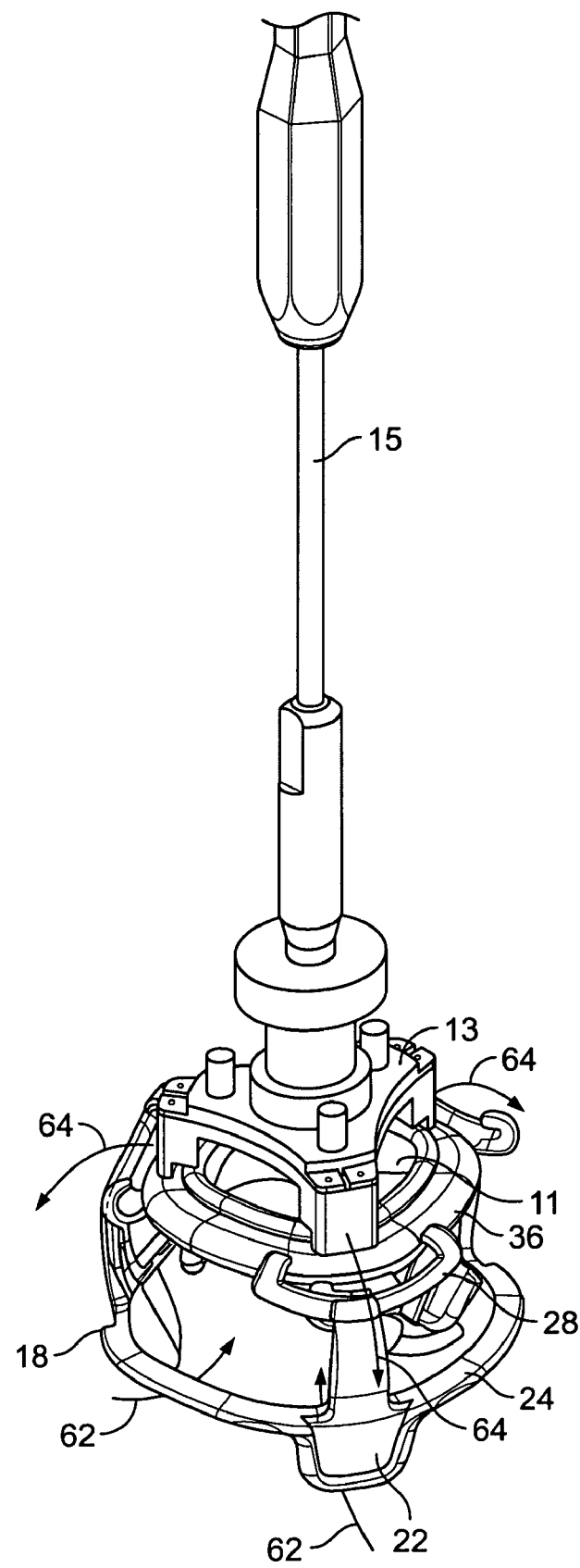
FIG. 6 shows an even later stage in the illustrative procedure depicted in part by FIGS. 3-5, together with related apparatus, all in accordance with this invention.

Once the rinse process is completed, finger tabs 22 below ring 24 are pressed toward the flow axis of the valve (illustrated by arrows 62) as shown in FIG. 6, rotating grips 28 away from sewing cuff 36 of heart valve 11 (illustrated by arrows 64). This releases heart valve 11 and valve holder 13 from support 18. Because support 18 was rinsed and sterilized with heart valve 11, the surgeon or scrub nurse is free to squeeze tabs 22 with his or her gloved hand.

Figure 7:
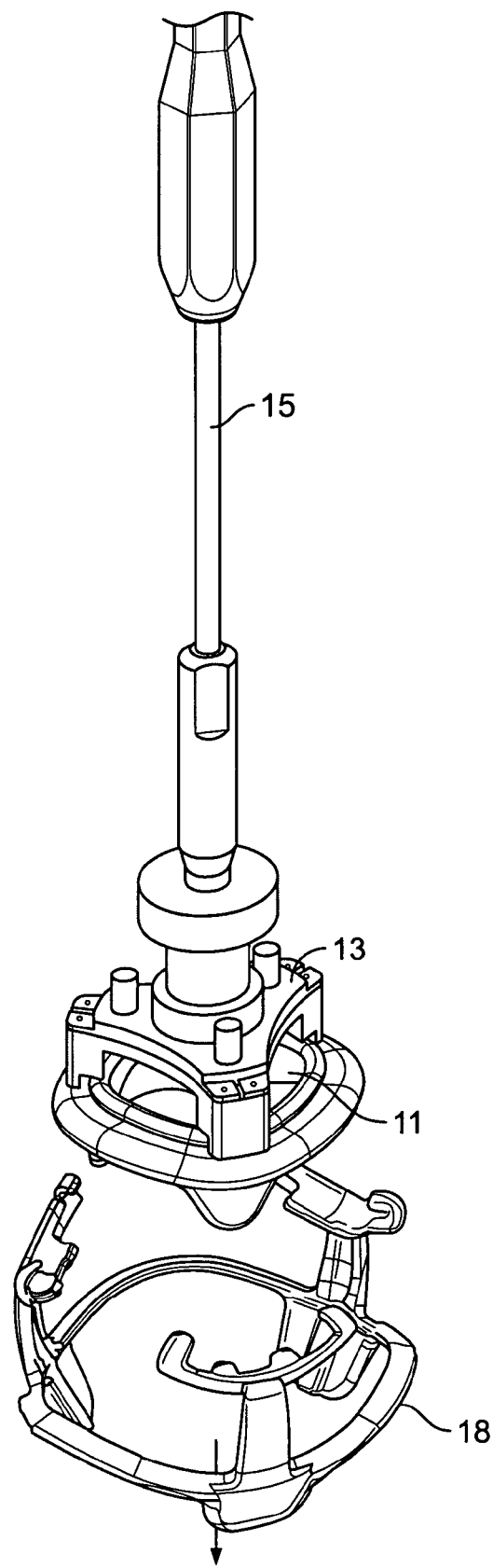
FIG. 7 shows an even later stage in the illustrative procedure depicted in part by FIGS. 3-6, together with related apparatus, all in accordance with this invention.
Figure 8:
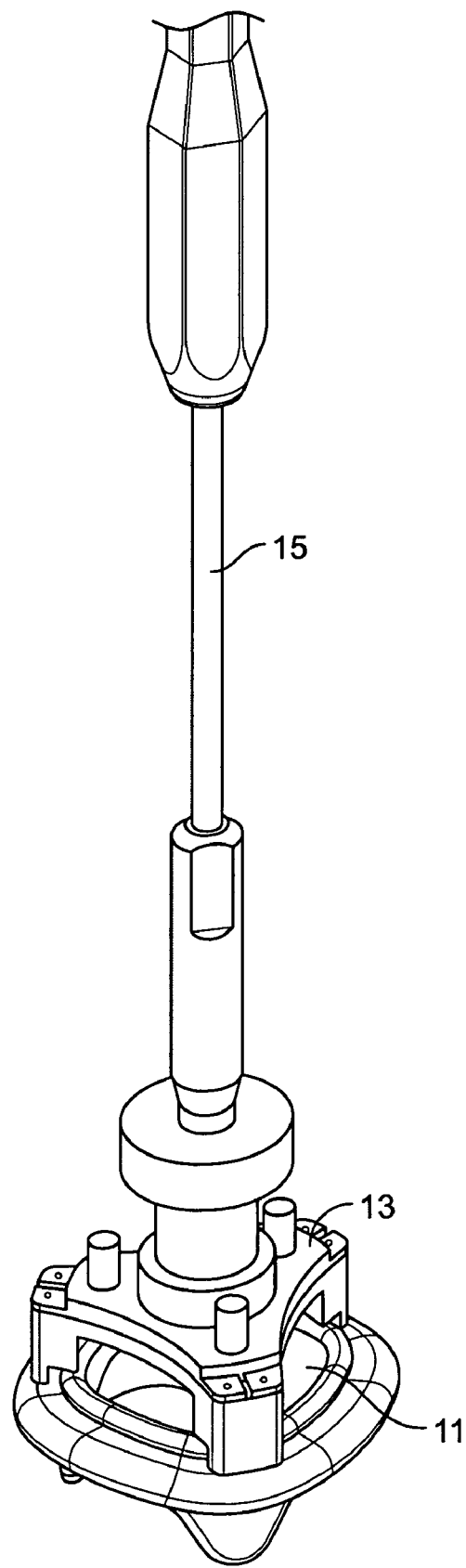
FIG. 8 shows an even later stage in the illustrative procedure depicted in part by FIGS. 3-7, together with related apparatus, all in accordance with this invention.
Figure 11:
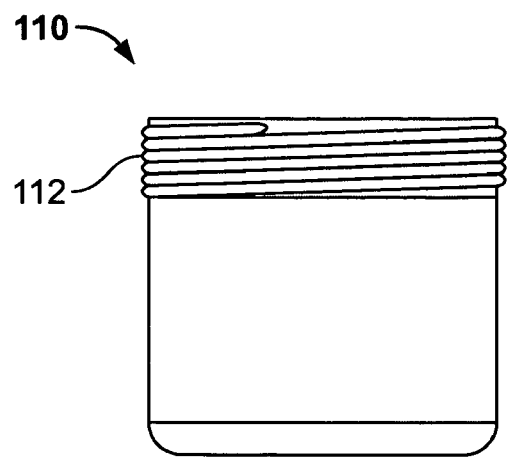
FIG. 11 is a perspective view of an illustrative embodiment of apparatus in accordance with the principles of the present invention.
Figure 12:
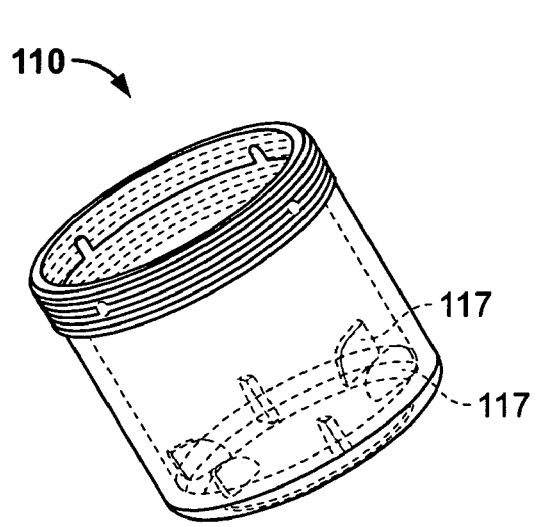
FIG. 12 is an isometric view of the apparatus shown in FIG. 11.
Figure 13:
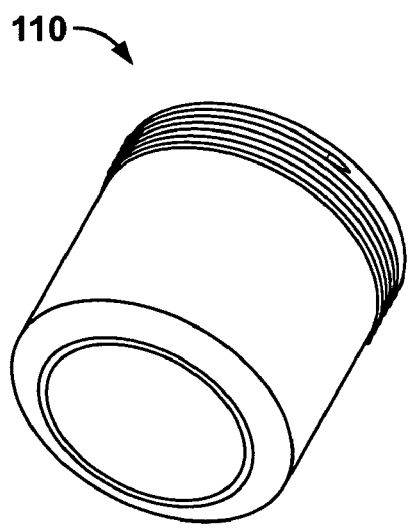
FIG. 13 is an isometric view of the apparatus shown in FIG. 11.
Figure 14:
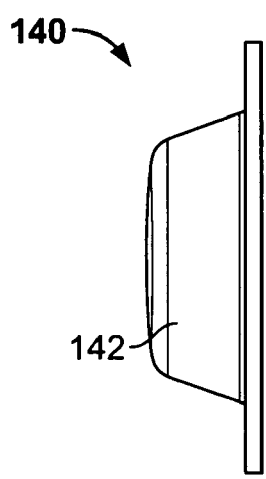
FIG. 14 is a perspective view of an illustrative embodiment of apparatus in accordance with the principles of the present invention.
Figure 15:
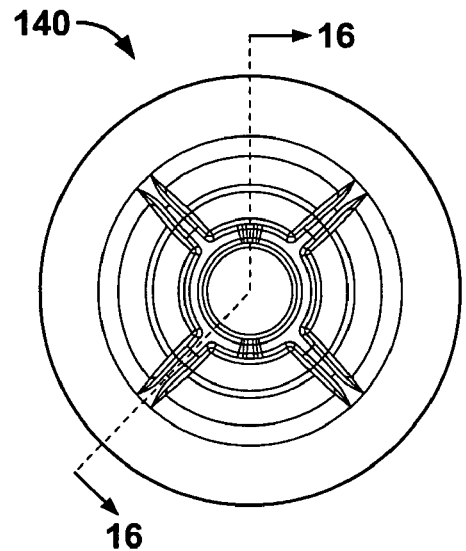
FIG. 15 is a view similar to FIG. 14 showing the apparatus illustrated in FIG. 14.

As shown in FIG. 7, support 18 is pulled away from heart valve 11 and valve holder 13. At this point, heart valve 11 and valve holder 13 are ready to be handed to the surgeon for installation in the patient in the assembly shown in FIG. 8. Holder handle 15 and valve holder 13 may be removed from the patient in one piece once the installation procedure is completed.

FIG. 9 shows a top-down view of jar 110, which is another illustration of a jar in accordance with the principles of the present invention, like jar 19 of FIG. 1. To prevent a valve/holder/support assembly, like assembly 50 of FIG. 5, from rotating in jar 110 when the handle is threaded into the valve holder, a number of tabs 117 may be added to the bottom of jar 110, like those shown in FIGS. 9 and 10. Tabs 117 interfere with the finger tabs on the heart valve support and prevent the valve/holder/support assembly from rotating freely in the jar.

FIGS. 9-13 show details of jar 110, including lid threads 112 and tabs 117.

A lid liner, such as lid liner 140 illustrated in FIGS. 14-18, may increase the effectiveness of the valve storage container. Lid liner 140 may be press fit into the lid of a jar like jar 19 and is removed from the jar when the lid is removed. When the lid is attached to the jar, cylindrical boss 142 extends from the lid liner into the jar and reduces the volume of storage solution in the jar. Due to these two factors, the fluid level in the jar is reduced to well below the rim of the jar when the lid is removed, greatly reducing the possibility of spilling storage solution in the operating room.

Figure 16:
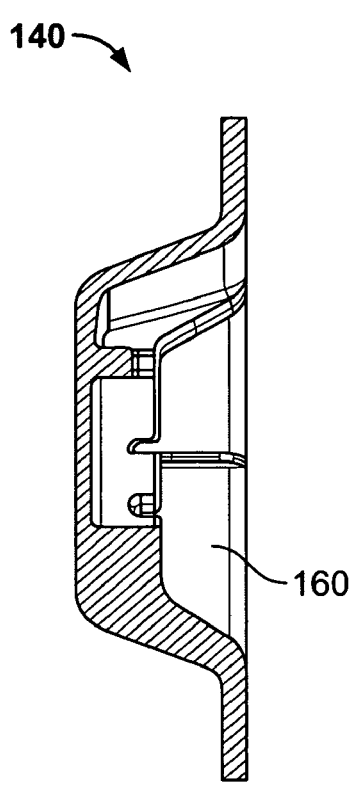
FIG. 16 is a cross-sectional view of the apparatus shown in FIG. 15 taken from line 16-16 of FIG. 15.
Figure 17:
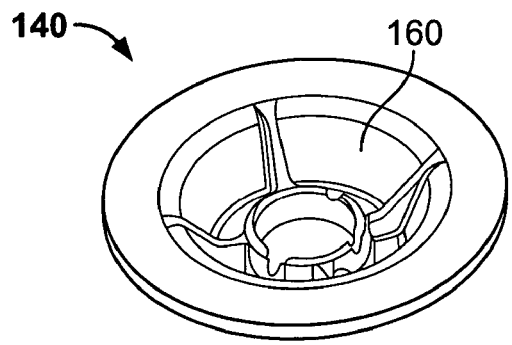
FIG. 17 is an isometric view of the apparatus shown in FIGS. 14-16.
Figure 18:
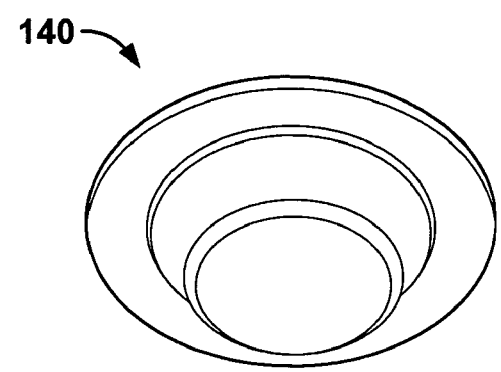
FIG. 18 is an isometric view of the apparatus shown in FIGS. 14-16.

Lid liner 140 may be used to vertically secure a valve/holder/support assembly in a jar and prevent damage during shipping. Cylindrical boss 142 of lid liner 140 may be hollowed out so that it is able to flex and secure valve/holder/support assemblies of varying heights. Hollow region 160 is shown in FIG. 16. FIGS. 14-18 show the details of a lid liner in accordance with the principles of the present invention.

FIGS. 19-33 illustrate the details of various embodiments of a heart valve support in accordance with the principles of the present invention. Specifically, FIGS. 19-23 show features of an aortic valve support, FIGS. 24-28 show features of a mitral valve support, and FIGS. 29-33 show features of a supra valve support. The support may be flexible so that one support can accommodate the entire size range for each type of heart valve, eliminating the need for supports of different sizes.

Figure 19:
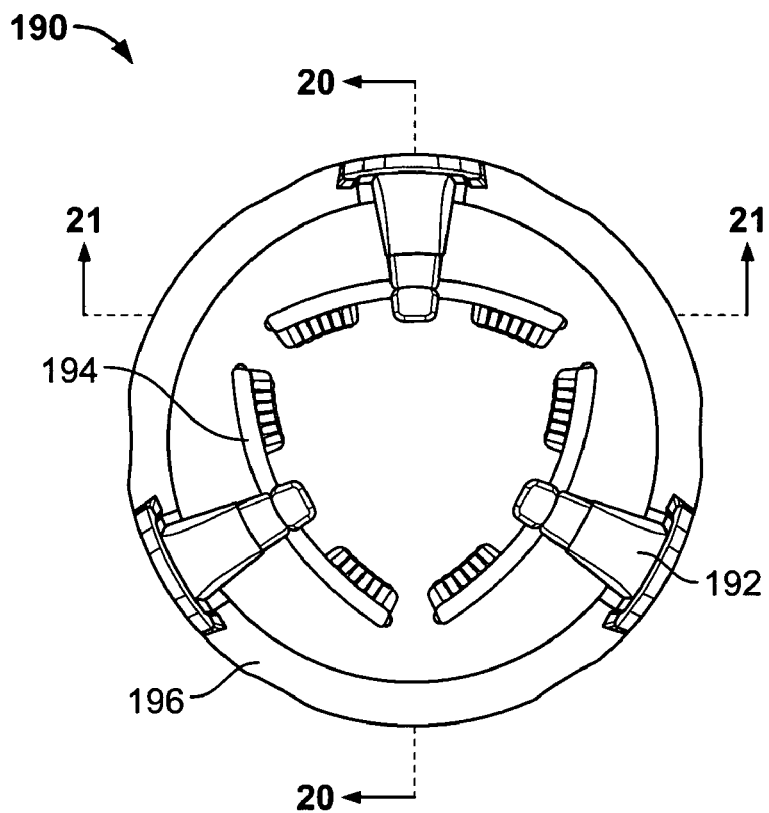
FIG. 19 is a perspective view of an illustrative embodiment of apparatus in accordance with the principles of the present invention.
Figure 20:
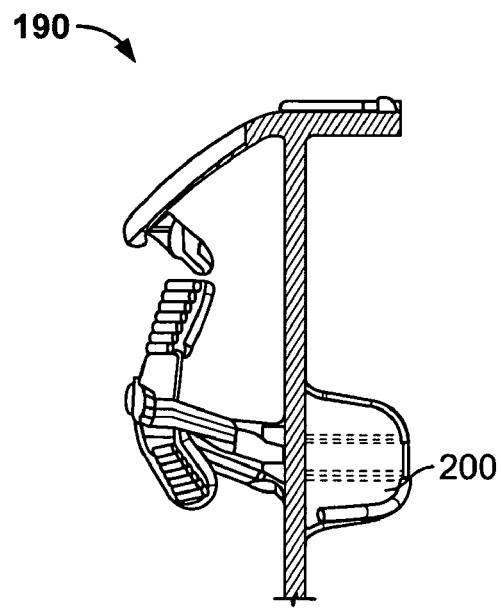
FIG. 20 is a cross-sectional view of the apparatus shown in FIG. 19 taken from line 20-20 of FIG. 19.

FIG. 19 shows aortic valve support 190. Aortic valve support 190 may have struts 192, grips 194, ring 196, and finger tabs 200 (see FIG. 20). Grips 194 may have torsional ridges 210 (see FIG. 21) that have been designed to fit within small grooves in the sewing cuff fabric and are asymmetric to preferentially resist handle tightening. Aortic support 190 engages the sewing cuff of a replacement aortic valve at locations annularly spaced around the valve.

Figure 24:
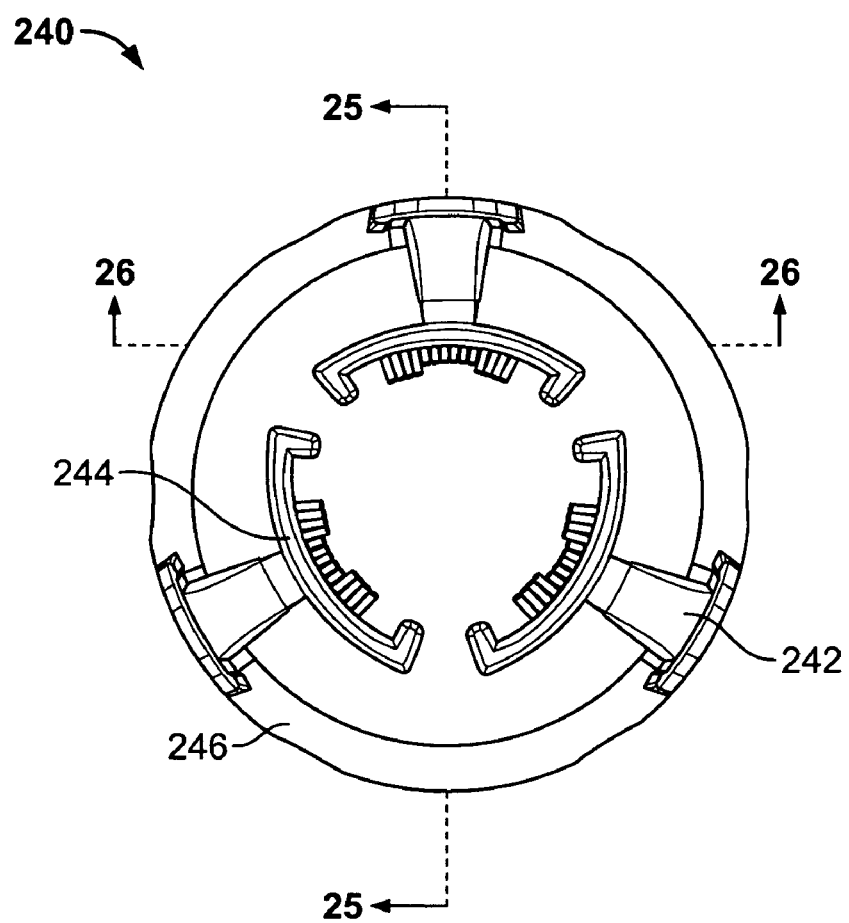
FIG. 24 is a perspective view of an illustrative embodiment of apparatus in accordance with the principles of the present invention.

FIG. 24 illustrates support 240, which may have special features adapted for supporting a replacement mitral valve. A holder, like valve holder 13 of FIG. 1, may engage a replacement mitral valve adjacent the sewing cuff in three areas that are spaced from one another annularly around the valve. Support 240 may engage the sewing cuff at locations that are annularly intercalated with and spaced from the locations at which the holder engages the valve.

Figure 25:
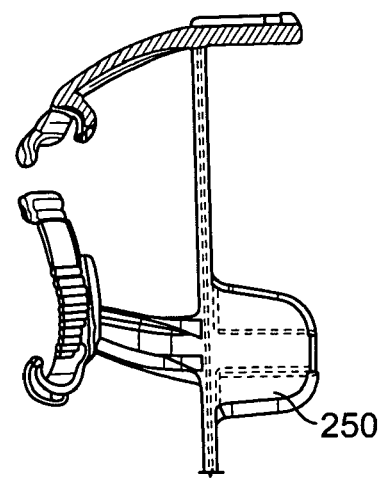
FIG. 25 is a cross-sectional view of the apparatus shown in FIG. 24 taken from line 25-25 of FIG. 24.
Figure 26:
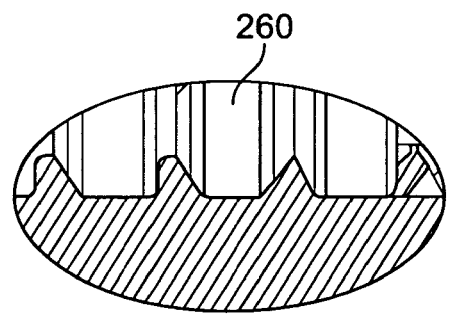
FIG. 26 is an enlarged detailed cross-sectional view of the apparatus shown in FIG. 24 taken from line 26-26 of FIG. 24.
Figure 27:
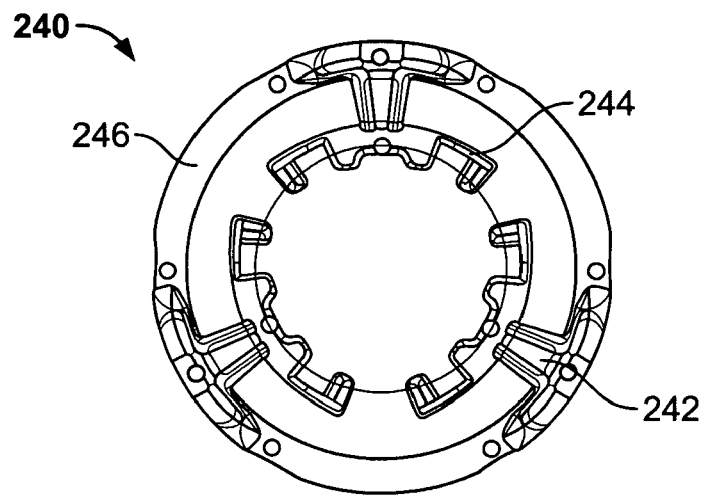
FIG. 27 is a perspective view of an illustrative embodiment of apparatus in accordance with the principles of the present invention.
Figure 28:
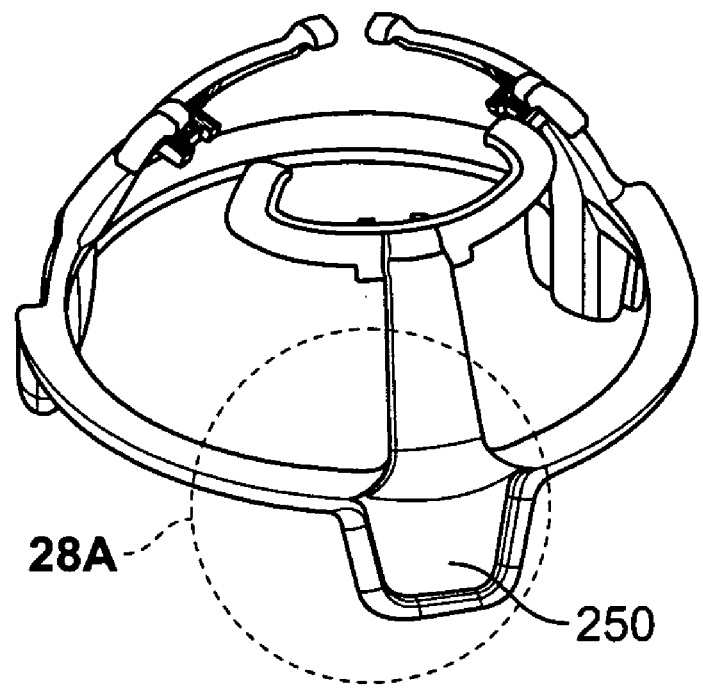
FIG. 28 is an isometric view of the apparatus shown in FIG. 27.
Figure 28A:
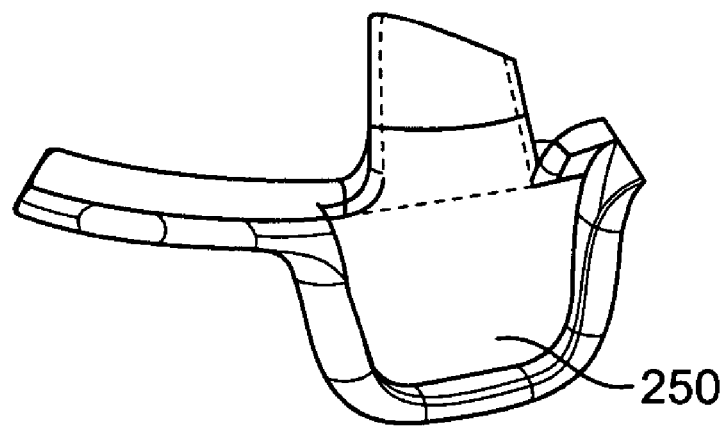
FIG. 28A is a view similar to FIG. 28 showing an enlarged view of detail A of FIG. 28.

Mitral valve support 240 may have struts 242, grips 244, ring 246, and finger tabs 250 (see FIG. 25). Grips 244 may have torsional ridges 260 (see FIG. 26) that have been designed to fit within small grooves in the sewing cuff fabric and are asymmetric to preferentially resist handle tightening. Mitral support 240 engages the sewing cuff of a replacement mitral valve at locations annularly spaced around the valve.

Figure 29:
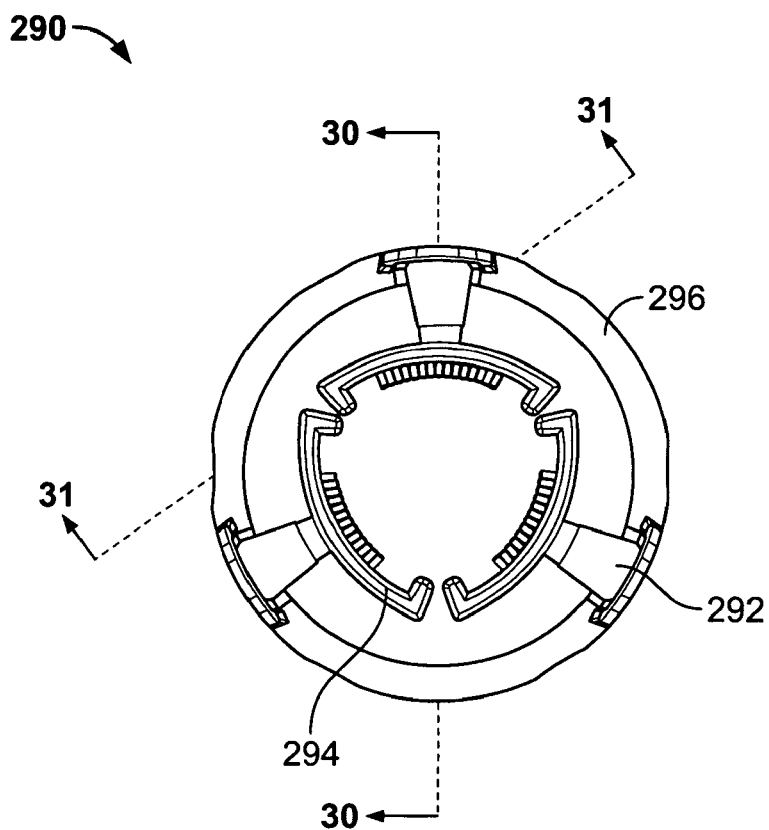
FIG. 29 is a perspective view of an illustrative embodiment of apparatus in accordance with the principles of the present invention.
Figure 30:
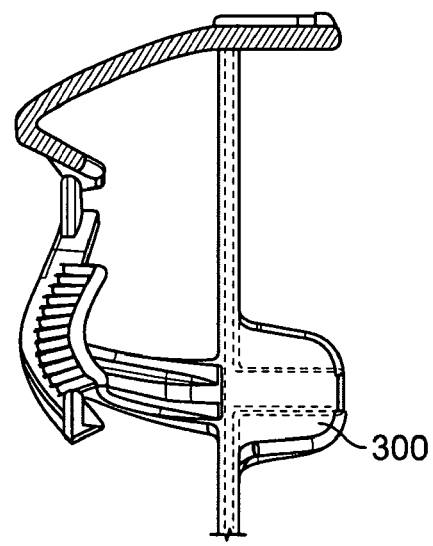
FIG. 30 is a cross-sectional view of the apparatus shown in FIG. 29 taken from line 30-30 of FIG. 29.
Figure 31:
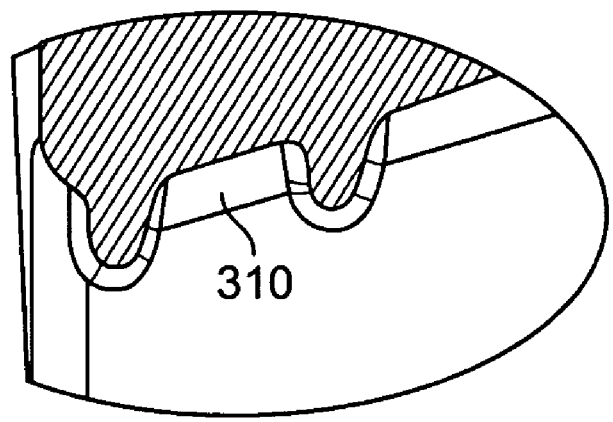
FIG. 31 is an enlarged detailed cross-sectional view of the apparatus shown in FIG. 29 taken from line 31-31 of FIG. 29.
Figure 32:
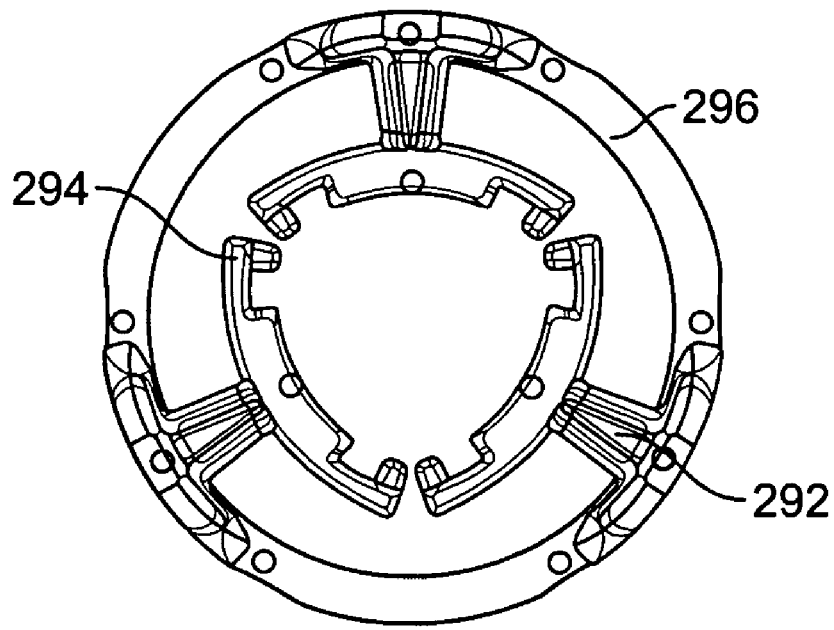
FIG. 32 is a perspective view of an illustrative embodiment of apparatus in accordance with the principles of the present invention.
Figure 33:
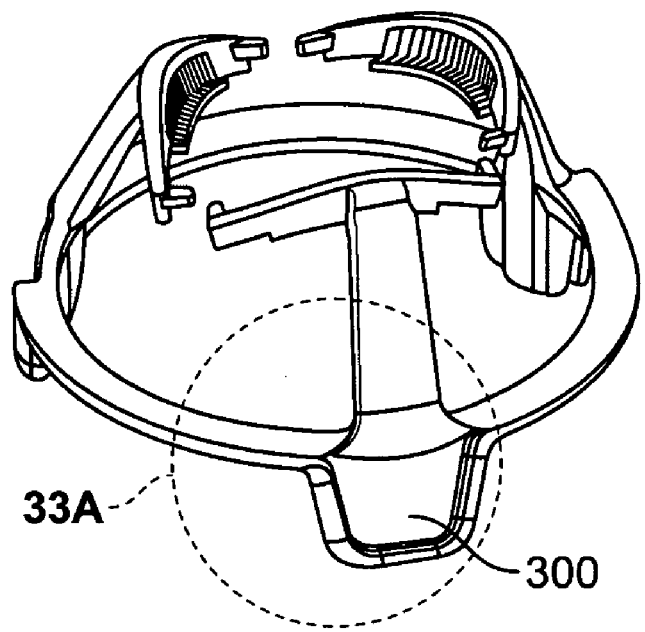
FIG. 33 is an isometric view of the apparatus shown in FIG. 32.
Figure 33A:
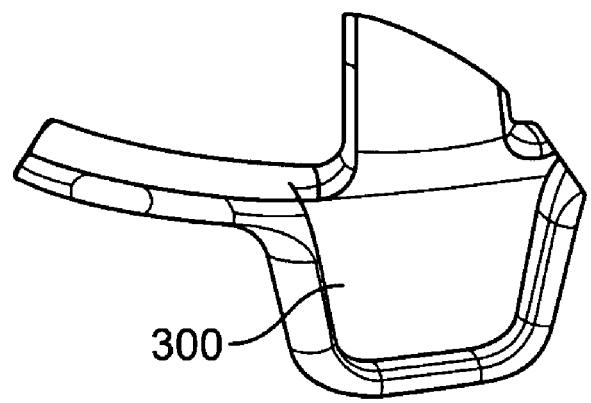
FIG. 33A is a view similar to FIG. 33 showing an enlarged view of detail A of FIG. 33.

FIG. 29 shows support 290 for engaging a supra replacement heart valve. Supra support 290 engages the sewing cuff of a replacement supra valve at locations annularly spaced around the valve, and may have struts 292, grips 294, ring 296, and finger tabs 300 (see FIG. 30). Grips 294 may have torsional ridges 310 (see FIG. 31) that have been designed to preferentially resist handle tightening.

As seen in FIGS. 19-33, various features of the struts, grips, rings, and tabs may be modified to support the various types of replacement heart valves. However, the basic structural principles of these support structures remain consistent in accordance with the principles of the present invention.

It will be understood that the foregoing is only illustrative of the principles of the invention, and that various modifications can be made by those skilled in the art without departing from the scope and spirit of the invention. For example, the order of some steps in the procedures that have been described are not critical and can be changed if desired. Also, various steps may be performed with various techniques.

What is claimed is:

1. Apparatus for storing a bioprosthesis submerged in a liquid storage solution comprising:
   a jar having a base, an annular side wall extending upwardly from the base, and an upper annular rim portion at the top of the annular side wall; and
   a lid removably mounted on the rim portion, the jar and the lid collectively comprising a container from which the storage solution cannot escape while the lid is on the jar, the lid having a centrally located boss that extends down into the jar below an upper edge of the annular side wall when the lid is on the jar, the boss shaped to prevent any of the storage solution in the jar from coming between any portion of the boss and remaining structure of the lid above the boss so that the boss reduces the volume of the jar that can contain the storage solution when the lid is on the jar.

2. The apparatus of claim 1 further comprising a support structure for the bioprosthesis, wherein the support structure is configured to rest on the base of the jar.

3. The apparatus of claim 2 further comprising a holder for the bioprosthesis.

4. The apparatus of claim 3 wherein the support structure and the holder are constrained by the base of the jar and the boss of the lid.

5. A method for storing a bioprosthesis comprising:
   suspending the bioprosthesis and a holder for the bioprosthesis, which is above and removably attached to the bioprosthesis, on a bioprosthesis support in a jar having a volume, the support being removably attached to the bioprosthesis and removable from the jar;
   filling the jar with a liquid storage solution; and
   closing the jar with a lid that cooperates with the jar to prevent escape of any of the storage solution while the jar is closed by the lid, the lid having a boss that extends downwardly into the jar below an upper annular edge of the jar when the lid is on the jar, and when the lid is on the jar, the boss performing the steps of:
      displacing a portion of the volume of the jar that would otherwise contain storage solution; and
      bearing down on the holder to keep the bioprosthesis and the support pressed down against a base of the jar.

6. Apparatus for supporting a bioprosthesis comprising:
   a holder releasably attached to the bioprosthesis; and
   a support structure configured to removably rest on a base of a storage container, the support structure including:
      a grip for releasably gripping the bioprosthesis to the support structure independently of the holder so that the bioprosthesis can be released from either one of the holder and the support structure while remaining attached to the other one of the holder and the support structure.

7. The apparatus of claim 6 wherein the support structure comprises a ring.

8. The apparatus of claim 7 wherein the support structure further comprises a strut coupling the grip to the ring.

9. The apparatus of claim 6 wherein the support structure comprises a support tab.

10. The apparatus of claim 9 wherein the support tab is configured to operate the grip.

11. The apparatus of claim 6 wherein the grip further comprises ridges configured to prevent movement of the bioprosthesis relative to the grip.

12. Apparatus for supporting a bioprosthesis comprising:
   a support structure configured to resting on a base of a storage container; and
   a grip operably attached to the support structure, wherein the grip is configured for gripping and releasing the bioprosthesis, wherein the support structure comprises a support tab, and
   wherein the support tab engages a tab on the base of the storage container.

13. A method for supporting a bioprosthesis in a storage container having a volume, a base, and a lid comprising:
   supporting the bioprosthesis from the base of the storage container with a support structure that is removable from the container and that is releasably attached to the bioprosthesis;
   releasably attaching a holder to the bioprosthesis above the support structure, the releasable attachment of the support structure to the bioprosthesis being independent of the releasable attachment of the holder to the bioprosthesis; and
   restraining the holder, the bioprosthesis, and the support structure between the base of the storage container and the lid of the storage container.

14. The method of claim 13 further comprising displacing a portion of the volume of the storage container with a boss extending downwardly from a central portion of the lid.

15. The method of claim 13 further comprising rotationally restraining the holder, the bioprosthesis, and the support structure with a tab on the base of the storage container.

* * * * *